US008097603B2

(12) United States Patent
Sirinyan et al.

(10) Patent No.: US 8,097,603 B2
(45) Date of Patent: Jan. 17, 2012

(54) COMPOSITIONS FOR CONTROLLING PARASITES ON ANIMALS

(75) Inventors: Kirkor Sirinyan, Bergisch Gladbach (DE); Andreas Turberg, Haan (DE)

(73) Assignee: Bayer Animal Health GmbH (DE)

( * ) Notice: Subject to any disclaimer, the term of this patent is extended or adjusted under 35 U.S.C. 154(b) by 979 days.

(21) Appl. No.: 10/555,298

(22) PCT Filed: Apr. 24, 2004

(86) PCT No.: PCT/EP2004/004359
§ 371 (c)(1),
(2), (4) Date: Nov. 2, 2005

(87) PCT Pub. No.: WO2004/098290
PCT Pub. Date: Nov. 18, 2004

(65) Prior Publication Data
US 2006/0252728 A1    Nov. 9, 2006

(30) Foreign Application Priority Data

May 8, 2003 (DE) .................................. 103 20 505

(51) Int. Cl.
*A01N 65/00* (2009.01)
(52) U.S. Cl. .............................. 514/66; 514/65; 424/405
(58) Field of Classification Search .................. 514/531, 514/65, 66; 424/405
See application file for complete search history.

(56) References Cited

U.S. PATENT DOCUMENTS

| 2,891,889 | A | * | 6/1959 | Haynes .......................... 424/45 |
| 4,668,666 | A | | 5/1987 | Allan et al. |
| 4,874,753 | A | | 10/1989 | Baker |
| 5,466,458 | A | | 11/1995 | Martin et al. |
| 5,612,047 | A | * | 3/1997 | Duffy et al. .................... 424/405 |
| 5,843,981 | A | | 12/1998 | Miller |
| 6,001,981 | A | | 12/1999 | DeAmicis et al. |
| 6,033,731 | A | | 3/2000 | Liebert et al. |
| 6,080,796 | A | | 6/2000 | Liebert et al. |
| 6,107,339 | A | * | 8/2000 | Katsuda et al. ............... 514/531 |
| 6,201,017 | B1 | | 3/2001 | Sembo et al. |
| 6,207,707 | B1 | * | 3/2001 | Teshima et al. ............... 514/531 |
| 6,335,357 | B1 | | 1/2002 | Okui et al. |
| 7,025,978 | B1 | | 4/2006 | Sirinyan et al. |
| 2002/0115565 | A1 | | 8/2002 | Asrar et al. |
| 2003/0073667 | A1 | | 4/2003 | Endris et al. |
| 2006/0211655 | A1 | | 9/2006 | Mencke et al. |

FOREIGN PATENT DOCUMENTS

| AU | 627847 | 9/1992 |
| AU | 666399 B | 3/1994 |
| EP | 137627 | 4/1985 |
| EP | 0375316 A1 | 6/1990 |
| EP | 413610 | 2/1991 |
| EP | 0 596 317 A1 | 5/1994 |
| GB | 2135886 | 9/1984 |
| JP | 63 126805 A | 5/1988 |
| JP | 7 196420 A | 8/1995 |
| WO | WO 86/03374 A1 | 6/1986 |
| WO | 91/13545 | 9/1991 |
| WO | 9507024 | 3/1995 |
| WO | 9851652 | 11/1998 |
| WO | 02077004 | 10/2002 |
| WO | 02077005 | 10/2002 |
| WO | WO 02/087338 A1 | 11/2002 |

OTHER PUBLICATIONS

Wang, I.-H. et al., "Simultaneous Determination of Dipropyl Pyridine-2,5-Dicarboxylate, N-octyl Bicycloheptene Dicarboximide, Piperonyl Butoxide, and Pyrethrins in Pet Shampoo by Reversed Phase High Performance Liquid Chromatography," Journal of Liquid Chromatography and Related Techonolgies, 1996, vol. 19, No. 20, p. 3293-3304.
Cochran, Donald, "Effects of Synergists on Bendiocarb and Pyrethrins Resistance in the German Cockroach (Dictyopter: Blattellidae)," Journal of Economic Entomology, Aug. 1987, vol. 80(4), pp. 728-732.
Cochran, Donald, "Effects of Three Synergists on Pyrethroid Resistance in the German Cockroach (Dictyoptera: Blattellidae)," Journal of Economic Entomology, Aug. 1994, vol. 87(4), pp. 879-884.
Cochran, Donald, "Selection for Pyrethroid Resistance in the German Cockroach (Dictyoptera: Blattellidae)," Journal of Economic Entomology, 1987, vol. 80(6), pp. 1117-1121.
Singh et al., "Synergism of MGK-264 and Piperonyl Butoxide on the Toxicity of Plant Derive Molluscicides," Chemosphere, 1998, vol. 36(15), pp. 3055-3060.
Tripathi et al, "Synergism in Tertiary Mixtures of Pesticides," Chemosphere, Nov. 1997, vol. 35(10), pp. 2365-2374.
Fao: 1967, Evaluations of some pesticide residues in food, The Monographs. MGK 264 (Food and Agriculture Organization of the United Nations, World Health organization, Rome, 1968). http://www.inchem.org/documents/jmpr/jmpmono/v067/pr25.htm.
Database Biosis 'Online! Biosciences Information Service, Philadelphia, PA, US; 1995, Onon Yoshihiro et al: "Synergistic Effect of Synthetic Synergists on Pyrethroids Against Adults of the Cat Flea Ctenocephalides Felts (Bouche)" XP002299303; Database accession No. PREV199698561306; Cited in the application, abstract.
Japanese Journal of Sanitary Zoology, vol. 46, No. 1, 1995, pp. 25-30, ISSN: 0424-7086 cited in the application .
Database WPI; Section CH, Week 199539; Derwent Publications Ltd., London, GB; AN 1995-299442; XP002299306.
Database Chemabs 'Online! Chemical Abstracts Service, Columbus, Ohio, US; XP002299304; retrieved from STN-International; Database accession No. 123:249228, abstract, Date: 1995.
R.H. Roberts et al.: "Effects of Additives on the Toxicity of Pyrethrins to Stable Flies and Horn Flies," Journal of Economic Entomology., vol. 56, No. 5, Oct. 1963, pp. 699-702, XP002299302, Usentomological Society of America, College Park, Maryland, p. 700; table 2.
Database Chemabs, 'Online! Chemical Abstracts Service, Columbus, Ohio, US; XP002299305, retrieved from STN-International; Database accession No. 109:124423, abstract, Date: 1988.
PCT International Search Report dated Oct. 27, 2004, 8 pgs.

* cited by examiner

*Primary Examiner* — Rebecca Prouty
*Assistant Examiner* — Danielle Sullivan

(57) ABSTRACT

The present invention relates to novel skin-friendly dermally applicable liquid formulations comprising a pyrethrin or pyrethroid and MGK 264 in a ratio of at least 1:20 and a further insecticide, preferably from the group of the neonicotinoids, for controlling parasitic arthropods on animals.

4 Claims, No Drawings

COMPOSITIONS FOR CONTROLLING PARASITES ON ANIMALS

This application is a 371 of PCT/EP2004/004359, filed Apr. 24, 2004.

The present invention relates to novel compositions for controlling parasites on animals, which compositions comprise a pyrethrin or pyrethroid and MGK 264; if appropriate, the compositions comprise a further insecticially and/or acaricidally active compound.

To apply active compounds, some of which are poorly water soluble, in the form of dermally applicable liquid formulations, it is necessary to prepare homogeneous solutions or emulsions based on organic solvents and insecticidally active compounds. For this purpose, the active compounds are in most cases dissolved in organic solvents, such as isopropanol, 2-butoxyethyl acetate or ethylene glycol diacetate, and, if appropriate, mixed with further additives. The preparation of such formulations is described in U.S. Pat. No. 4,874,753, EP-A 137 627 and GB 2 135 886. The disadvantages of said systems are, for example when active compounds from the class of the pyrethrins and pyrethroids, in particular α-cyanopyrethroids, are used, that they cause severe skin irritations and, furthermore, have only a short long-term action. It is desirable to replace these formulations by formulations which are skin-friendly and toxicologically acceptable and have a long-term action of several weeks.

To overcome said disadvantage of, for example, the known pyrethroids and pyrethrins, AU-627 847 and EP-A 413 610 propose to dissolve these active compounds in high-boiling solvents such as monopropyleneglycol which additionally also comprise natural skin-friendly oils such as pine oil, sunflower oil or soya oil. WO 91/13545 discloses that it is possible to prepare skin-friendly liquid formulations with good activity by dissolving said active compounds in amounts of >50% in aliphatic solvents such as 2-(2-butoxyethoxy)ethanol or 2-(2-methoxyethoxy)ethanol. The disadvantage of these formulations is that they require the use of relatively large amounts of active compound and that they also cause skin irritations in sensitive animal breeds. To achieve an acceptable biological action using small amounts of active compound, the U.S. Pat. No. 5,466,458 proposes the use of emulsions based on said active compounds with long-chain aliphatic amines or alcohols such as hexadecan-1-ol or 1-octadecylamine. The use of long-chain amines has the disadvantage that they degrade said active compounds over time. In most cases, the formulations based on long-chain alcohols have insufficient long-term action.

Furthermore, WO 01/35739 proposes to combine pyrethroids, in particular α-cyanopyrethroids, which are critical with respect to skin irritation, with polysiloxanes which additionally comprise quaternary ammonium groups. However, this elegant form of preparation has the disadvantage that it requires the use of relatively large amounts of pyrethroid. In many cases, this fact may result in incompatibility with the target animal or the environment.

The literature states that synthetic or natural pyrethroids can be combined with organic synergists such as piperonyl butoxide (PBO), (2-(2-ethylhexyl)-3a,4,7,7a-tetrahydro-4,7-methano-1H-isoindole-1,3(2H)-dione (MGK 264), S,S,S-tributylphosphorotrithioate (DEF) or Synepirin [see, for example, JOURNAL OF ECONOMIC ENTOMOLOGY, (1994 August) 87 (4) 879-84, 1994), JOURNAL OF ECONOMIC ENTOMOLOGY, (1987 August) 80 (4) 728-32 or India Chemsphere, (November, 1997) Vol. 35, No. 10, pp. 2365-2374. ISSN: 0045-6535, Japanese Journal of Sanitary Zoology, (1995) Vol. 46, No. 1, pp. 25-30. ISSN: 0424-7086. 1995 and also J ECON ENTOMOL, (1987) 80 (6), 1117-1121. CODEN: JEENAI. ISSN: 0022-0493. 1987)]. The literature mentioned above also states that the activity of the pyrethroid-containing preparations against adult fleas can be improved by combining pyrethroids with said synergists in amounts of from 1:5 to at most 1:20. The literature [see, for example, DEP. ENTOMOL., UNIV. GEORGIA, COASTAL PLAIN EXP. STN., TIFTON, GA. 31793 or India Chemosphere, (1998) 36/15 (3055-3060) 1998] states, that maximum improvement of activity is achieved at a ratio of active compound to synergist of 1:5 (for example in the case of permethrin/MGK-264 or fenvalerate/PBO).

Furthermore, it is known that shampoos comprising dipropyl pyridine-2,5-dicarboxylate, MGK 264, piperonyl butoxide, and pyrethrins can be used for controlling fleas on small animals [see, for example, Wang I.-H.; Moorman R.; Burleson J. I.-H. Wang, Journal of Liquid Chromatography and Related Technologies, (1996) 19/20 (3293-3304)].

It is furthermore known that carbamates such as propoxur in combination with PPO and MGK 264 in ratios of 1.00:0.04:0.1 are suitable for treating habitats (see, for example, the company prospectus from Sano Bruns Enterprises Ltd. Israel, 1990 AO1N-047/44).

U.S. Pat. No. 0,124,306, 1999, describes combinations of imidacloprid and/or fipronil and/or pyrethroids for controlling pests in agriculture. Furthermore, EP-A-981 956 (U.S. Pat. No. 6,080,796) describes foams based on the abovementioned active compounds, and the patent application EP-A-981 955 (U.S. Pat. No. 6,033,731) describes polymer alloys prepared from suspensions or emulsions of the active compounds imidacloprid and permethrin, for controlling parasites.

All of the preparation forms mentioned have the disadvantage that, in an acceptable application form, they are not suitable for controlling ectoparasites, such as fleas, ticks and mosquitoes, for a duration of at least three, but preferably four, weeks, and that they furthermore require the use of relatively large amounts of active compound.

It is an object of the present invention to provide compositions comprising pyrethroids or pyrethrins, which compositions are suitable for controlling parasites, preferably ectoparasites, on animals. Such preparations have high parasiticidal activity and are well tolerated by the animal treated. In addition, good user compatibility and environmental compatibility are also important. It should be possible to produce liquid preparations allowing the elegant spot-on application.

Surprisingly, this object is achieved by employing pyrethroids and/or pyrethrins, in particular α-cyanopyrethroids, in combination with the synergist MGK 264 in amounts of at least 1:20, in contrast to current teaching.

Surprisingly, using the ratios of at least 1:20 according to the invention, a considerably improved target animal and user compatibility and an enormous activity-enhancing synergistic effect are achieved.

Accordingly, the invention relates to compositions, comprising
a) at least one active compound from the compound class of the pyrethroids and/or the compound class of the pyrethrins
b) MGK 264
in a weight ratio of components a:b of at least 1:20,
and also
c) if appropriate, further active compounds and
d) if appropriate further auxiliaries and carriers.

In general, the pyrethrins are employed in combination with a pyrethroid.

The compositions according to the invention are preferably fluid or liquid and are particularly highly suitable for preparing spot-on and pour-on formulations for use in parasite control on animals.

Suitable active compounds (component a) which are to be emphasized are the pyrethrins and the pyrethroids, such as, for example: fenvalerate [α-cyano-3-phenoxybenzyl α-(p-Cl-phenyl)isovalerate], flumethrin [(α-cyano-4-fluoro-3-phenoxy)benzyl 3-[2-4-chlorophenyl)-2-chlorovinyl]-2,2-dimethylcyclopropanecarboxylate] and its enantiomers and stereoisomers, cyfluthrin [(α-cyano-4-fluoro-3-phenoxy)benzyl 2,2-dimethyl-3-2,2-dichlorovinyl)cyclopropanecarboxylate], permethrin [3-phenoxybenzyl cis,trans-3-2,2-dichlorovinyl)-2,2-dimethylcyclopropanecarboxylate], cypermethrin [α-cyano-3-phenoxybenzyl 2,2-dimethyl-3-(2,2-dichlorovinyl)cyclopropanecarboxylate], deltamethrin [α-cyano-3-phenoxybenzyl cis,trans-3-2,2-dibromovinyl)-2,2-dimethylcyclopropanecarboxylate], fluvalinate [2-cyano-3-phenoxybenzyl 2-(2-chloro-α,α,α-trifluoro-p-toluido)-3-methylbutyrate]. Preference is given to using pyrethroids having acaricidal action. Particularly preferred are the α-cyanopyrethroids, in particular the esters of α-cyano-3-phenyl-benzyl alcohols and 4-fluoro-L-cyano-3-phenoxybenzyl alcohols. Among these, particular preference is given to flumethrin, cyfluthrin and β-cyfluthrin.

In the compositions according to the invention, the pyrethrins and/or pyrethroids are usually present in amounts of 0.01-20% by weight, preferably 0.05-5.0% by weight, particularly preferably 0.075-0.75% by weight, very particularly preferably 0.10-0.50% by weight, based in each case on the weight of the finished composition. In the case of spray applications, the concentrations are usually lower, namely preferably in the range of from 0.02 to 0.1% by weight, particularly preferably 0.03 to 0.1% by weight, very particularly preferably 0.03 to 0.075% by weight.

The ratio by weight of the amount of pyrethrin and/or pyrethroid to the amount of MGK 264 is at least 1:20 (here, "at least" means that the proportion of MGK 264 in the ratio to pyrethrin/pyrethroid may also be higher), preferably 1:30, particularly preferably 1:40. Usually, the ratio is adjusted to be not more than 1:100, preferably 1:80, particularly preferably 1:60.

Of course, the compositions according to the invention may also comprise, as combination partners, further active compounds.

Preferred active compounds for combinations which may be mentioned are insecticides used for controlling ectoparasitic arthropods, such as neonicotinoid insecticides, spinosyns, N-phenylpyrazoles, carbamates, phosphoric and phosphonic esters, growth inhibitors and also mixtures of these active compounds with one another. It is also possible to add further synergists. For the purpose of this application, synergists are to be understood as meaning compounds which for their part do not have the desired activity but, as mixing partners, enhance the activity of the active compounds.

Neonicotinoid insecticides which may be mentioned are compounds of the formulae (I), (II) and (III):

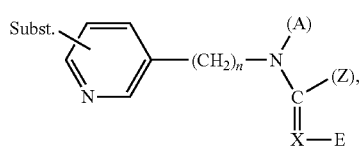

(I)

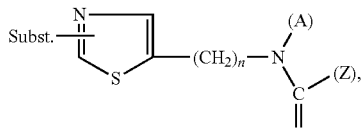

(II)

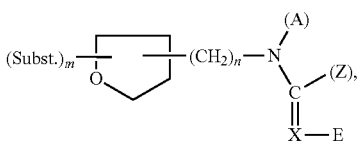

(III)

in which
n represents 1 or 2,
m represents 0, 1 or 2,
Subst. represents one of the substituents listed above, preferably halogen, particularly preferably chlorine,
A represents a monofunctional group from the group consisting of hydrogen, acyl, alkyl and aryl or represents a bifunctional group which is attached to the radical Z;
E represents an electron-withdrawing radical;
X represents the radicals —CH= or =N—, where the radical —CH= may be attached instead of an H atom to the radical Z;
Z represents a monofunctional group from the group consisting of alkyl, —O—R, —S—R and

or represents a bifunctional group which is attached to the radical A or the radical X.

Preference is given to compounds of the formulae (I), (II) and (III), where the radicals are as defined below:
A particularly preferably represents hydrogen and optionally substituted radicals from the group consisting of $C_1$-$C_8$-acyl, $C_1$-$C_{10}$-alkyl, $C_6$-$C_{10}$-aryl. A furthermore represents a bifunctional group. Mention may be made of optionally substituted alkylene having 1-4, in particular 1-2, C atoms, suitable substituents being the substituents listed further above, where the alkylene groups may be interrupted by one or two identical or different heteroatoms from the group consisting of N, O and S.
A and Z together with the atoms to which they are attached may form a saturated or unsaturated heterocyclic ring. The heterocyclic ring may contain a further 1 or 2 identical or different heteroatoms and/or hetero groups. Preferred heteroatoms are oxygen, sulphur or nitrogen, and preferred hetero groups are N-alkyl groups, where the alkyl of the N-alkyl group preferably contains 1 to 4, in particular 1 or 2, carbon atoms. Alkyl groups which may be mentioned are methyl, ethyl, n- and i-propyl and n-, i- and t-butyl. The heterocyclic ring contains 5 to 7, preferably 5 or 6, ring members.
Examples of the heterocyclic ring which may be mentioned are pyrrolidine, piperidine, piperazine, hexamethyleneimine, hexahydro-1,3,5-triazine and morpholine which, if appropriate, may be substituted, preferably by methyl.
E represents an electron-withdrawing radical; mention may be made in particular of $NO_2$, CN, haloalkyl carbonyl, and in particular having 1-4 carbon atoms and 1 to 5 halogen atoms, such as, for example, COCF$_3$.

X represents —CH= or —N=.

Z represents optionally substituted radicals C$_1$-C$_{10}$-alkyl, —OR, —SR, —NRR, where the substituents are preferably as defined under R.

Z may, in addition to the abovementioned ring, together with the atom to which it is attached and the radical

instead of X form a saturated or unsaturated heterocyclic ring. The heterocyclic ring may contain a further 1 or 2 identical or different heteroatoms and/or hetero groups. Preferred heteroatoms are oxygen, sulphur or nitrogen, and preferred hetero groups are N-alkyl groups, where the alkyl or N-alkyl group preferably contains 1 to 4, in particular 1 or 2, carbon atoms. Alkyl groups which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methylpiperazme.

R represents hydrogen and also represents optionally substituted radicals from the group consisting of acyl, alkyl, aryl, aralkyl, heteroaryl, heteroarylalkyl.

Acyl radicals which may be mentioned are formyl, alkylcarbonyl, arylcarbonyl, alkylsulphonyl, arylsulphonyl, (alkyl)(aryl)phosphoryl, which for their part may be substituted.

Alkyl groups which may be mentioned are C$_{1-10}$-alkyl, in particular C$_{1-4}$-allyl, specifically methyl, ethyl, isopropyl, sec- or tert-butyl, which for their part may be substituted.

Aryl groups which may be mentioned are phenyl and naphthyl, in particular phenyl.

Aralkyl groups which may be mentioned are phenylmethyl and phenethyl.

Heteroaryl groups which may be mentioned are heteroaryl groups having up to 10 ring atoms and, as heteroatoms, N, O, S, in particular N. Specific mention may be made of thienyl, furyl, thiazolyl, imidazolyl, pyridyl, benzothiazolyl.

Heteroarylalkyl groups which may be mentioned are heteroarylmethyl, heteroarylethyl having up to 6 ring atoms and, as heteroatoms, N, O, S, in particular N.

Substituents which may be mentioned are, by way of example and preferably:

alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy, alkylthio having preferably 1 to 4, in particular 1 or 2, carbon atoms, such as methylthio, ethylthio, n- and i-propylthio and n-, i- and t-butylthio; haloalkyl having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methylethylamino, n- and i-propylamino and methyl-n-butylamino; carboxyl; carbalkoxy having preferably 2 to 4, in particular 2 or 3, carbon atoms, such as carbomethoxy and carboethoxy; sulpho (—SO$_3$H); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and also heteroarylamino and heteroarylalkylamino, such as chloropyridylamino and chloropyridylmethylamino.

Very particular preference is given to compounds of the formulae (I), (II) and (III) in which N represents 1, m represents 0, Subst. represents chlorine, A represents hydrogen or C$_{1-3}$-alkyl, Z represents C$_{1-3}$-alkyl, —NH$_2$, —NH(C$_{1-3}$-alkyl) or —N(C$_{1-3}$-alkyl)$_2$, or A and Z together with the atoms to which they are attached form a saturated 5- or 6-membered heterocyclic ring which contains 1 or 2 identical or different heteroatoms or hetero groups selected from the group consisting of O, S, —NH—, and —N(C$_{1-3}$-alkyl), X represents —CH= or =N—, E represents —NO$_2$ or CN.

Specifically, the following compounds may be mentioned:

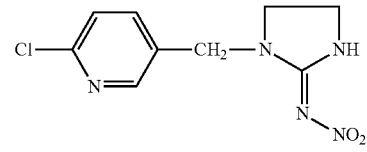

imidacloprid

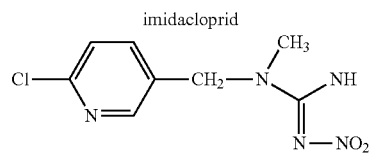

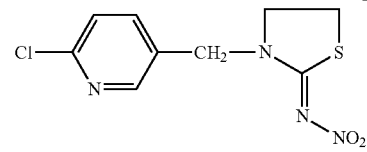

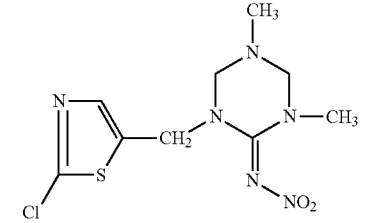

AKD 1022

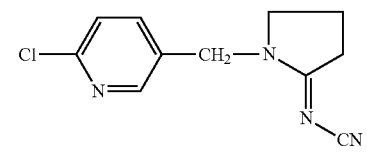

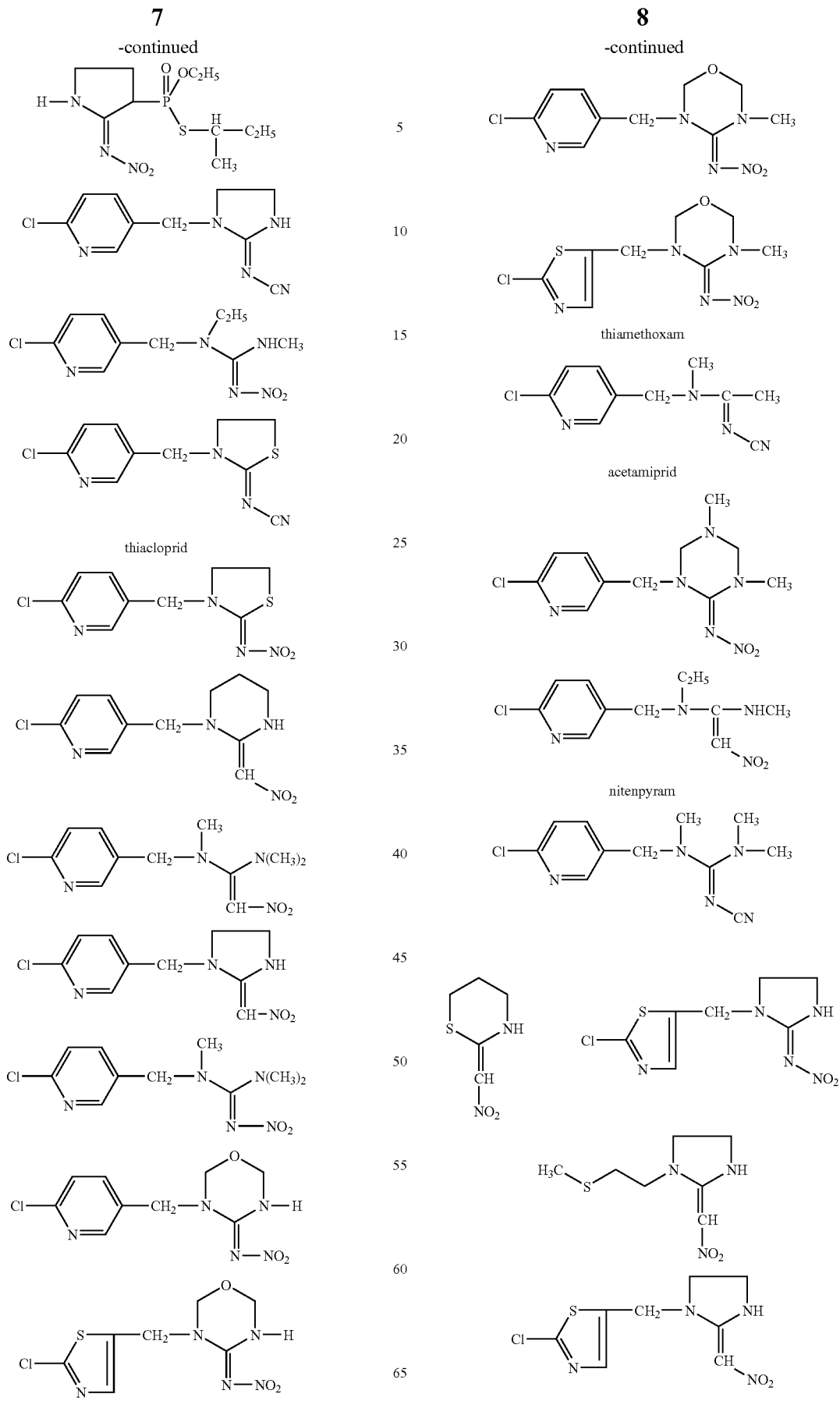

-continued
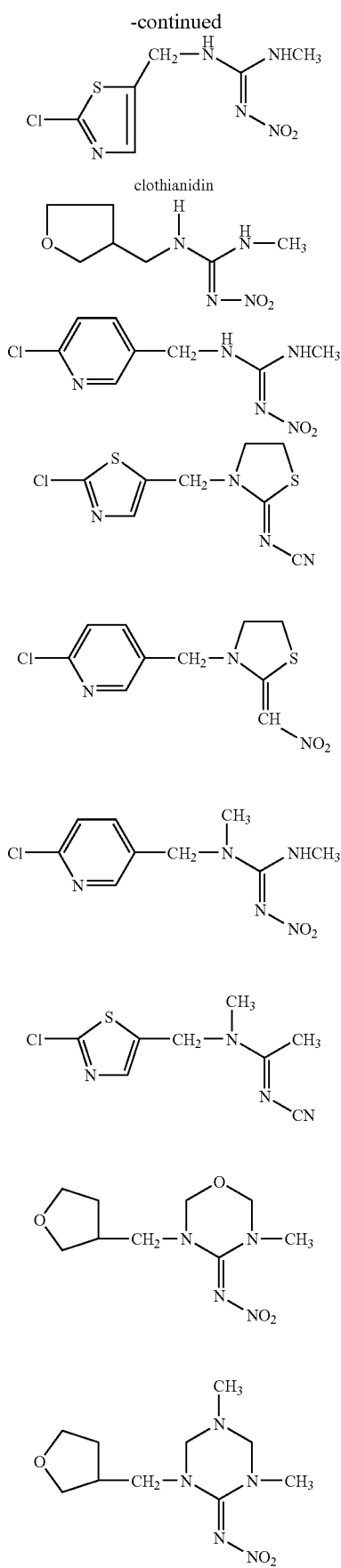
Particular emphasis is given to the compounds
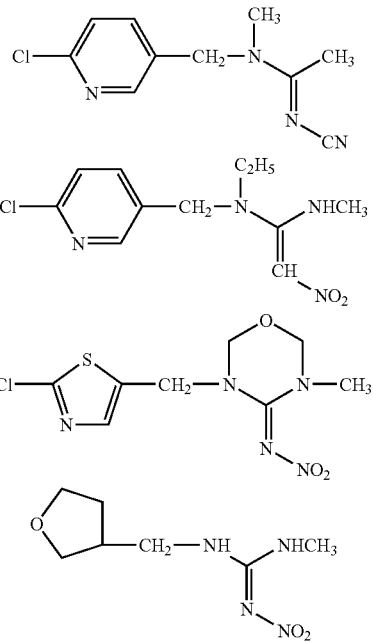
Particular emphasis is furthermore given to the compounds
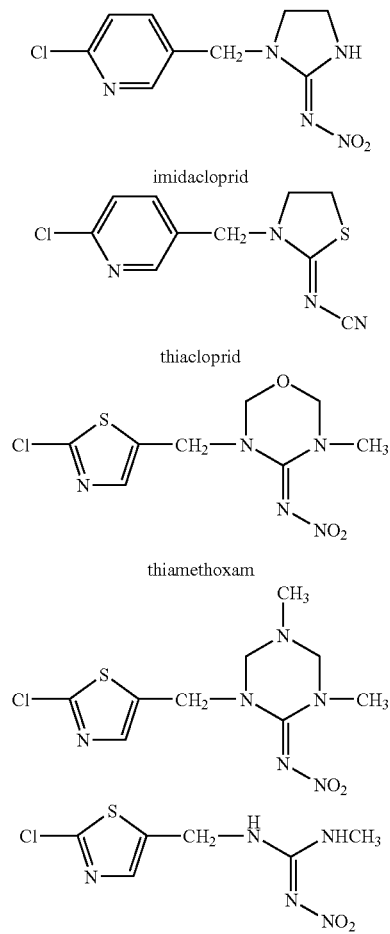

Spinosyns which may be mentioned here are, in particular, spinosyns A and D

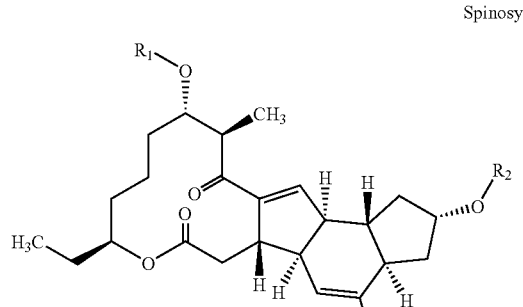

Spinosyn A

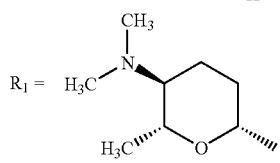

Spinosyn D

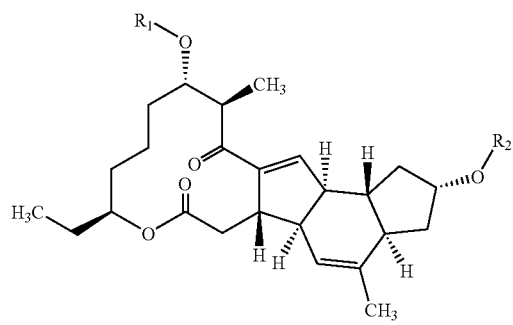

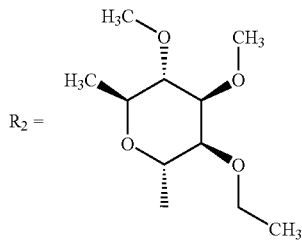

as described in Boeck et al. in EP-375 316 A1 and Deamicis et al. in WO 97/00265 A1.

Here, spinosyns are also understood as including synthetic and semisynthetic derivatives of natural spinosyns or derivatives obtained from genetically modified strains of; for example, *Saccharopolyspora* species, as described, for example, in WO 02/77004 and WO 02/77005.

By way of example, compounds of the formulae (IV) and (V) may be mentioned in which $R_3$ is a glycoside ($R_3=R_1$), $R_4$ is H, OH or alkoxy; $R_5$ is H, methyl, $R_6$ and $R_7$ are H or combined to a double bond or an epoxy group, $R_8$ in formula (IV) is trans-1-butenyl, 1,3-butadienyl, butyl, 3-hydroxybutenyl, propyl, 1-propenyl, 1,2epoxy-1-butyl, 3-oxo-1-butenyl, $CH_3CH(OCH_3)CH=CH—$, $CH_3CH=CHCH(CH_2CO_2CH_3)—$, or $CH_3CH=CHCH[CH_2CON(CH_3)]—$; $R_9$ is H or a glycoside ($R_9=R_2$).

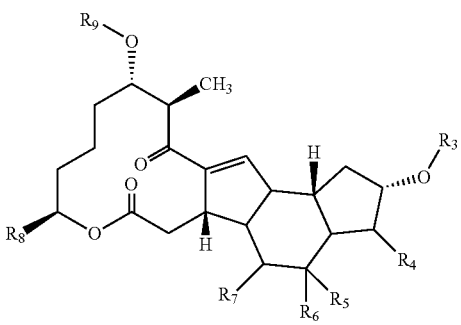
(IV)

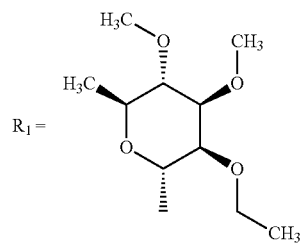

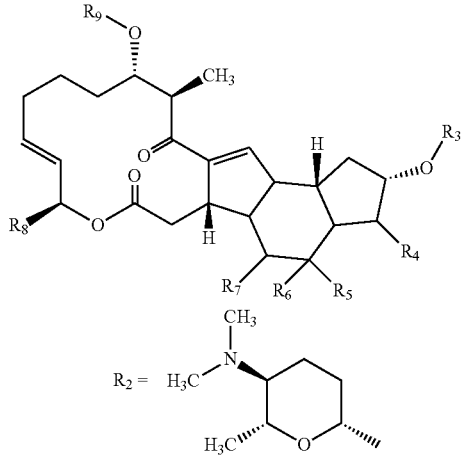
(V)

Phenylpyrazoles which may be mentioned are, for example, the following compounds:

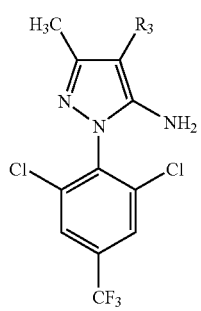
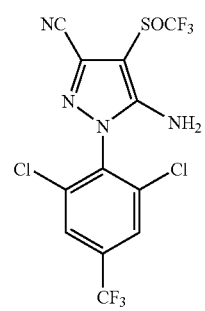
fipronil

-continued

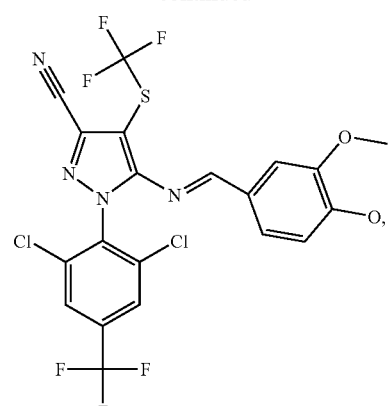

vanilliprole

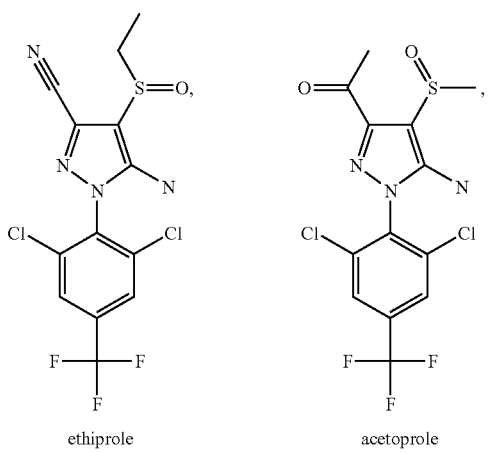

ethiprole      acetoprole

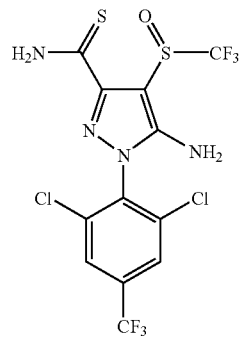

and compounds from WO 98/45274 for example of the type

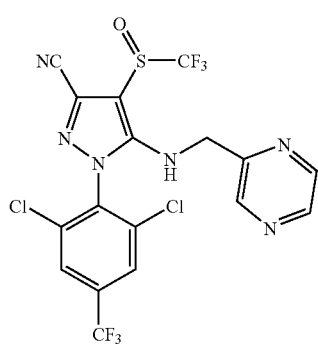

-continued

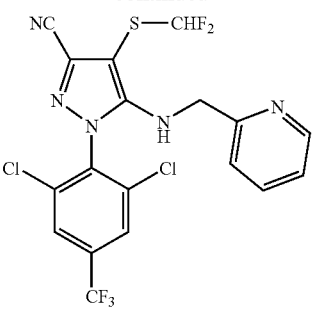

Carbamates which may be mentioned are substituted phenyl carbamates and naphthyl carbamates, preferred examples being:

2-oxobutylphenyl N-methylcarbamate,
4-dimethylamino-3-methylphenyl N-methylcarbamate,
2-isopropoxyphenyl N-methylcarbamate,
1-naphthyl N-methylcarbamate,
m-tolyl N-methylcarbamate,
3,4-xylyl N-methylcarbamate,
3,5-xylyl N-methylcarbamate,
2-[1,3-dioxolan-2-yl]phenyl N-methylcarbamate.

Phosphoric acid esters which may be mentioned as being preferred are the compounds having the common names phoxim, fenitrothion, dichlorvos, trichlorfon and malathion.

Juvenile hormones and juvenile-hormone-like compounds are, for example, the following:

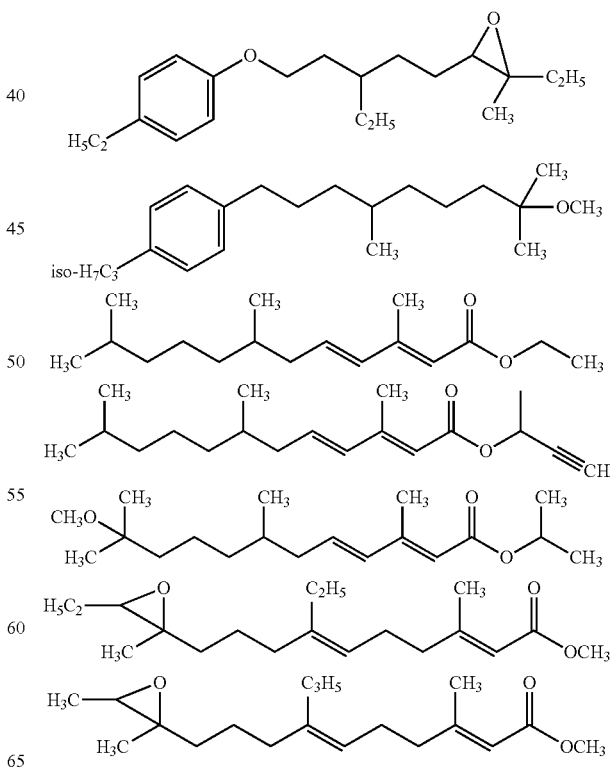

Substituted diaryl ethers are, for example, the following compounds:

| R$^1$ | R$^3$ | R$^5$ | R$^6$ | Z |
|---|---|---|---|---|
| H | H | CH$_3$ | 2-Cl | O |
| 5-F | H | CH$_3$ | H | O |
| H | H | CF$_3$ | H | O |
| H | H | C$_2$H$_5$ | H | O |
| H | H | H | H | O |
| H | H | CH$_3$ | H | CH$_2$ |
| H | H | CH$_3$ | H | C(CH$_3$)$_2$ |

Benzoylureas are, for example, the following compounds:

| R$^1$ | R$^2$ | R$^4$ |
|---|---|---|
| H | Cl | CF$_3$ |
| Cl | Cl | CF$_3$ |
| F | F | CF$_3$ |
| H | F | CF$_3$ |
| H | Cl | SCF$_3$ |
| F | F | SCF$_3$ |
| H | F | SCF$_3$ |
| H | Cl | OCF$_3$ |
| F | F | OCF$_3$ |
| H | F | OCF$_3$ |
| F | F | O—C$_6$H$_4$—Cl |
| F | F | O—C$_6$H$_4$—CF$_3$ |
| F | F | O—C$_6$H$_4$—CF$_3$ |

Triazines are, for example, the following compounds:

| R$^1$ | R$^2$ | R$^3$ |
|---|---|---|
| cyclopropyl | H | H |
| cyclopropyl | H | CH$_3$ |

-continued

| R$^1$ | R$^2$ | R$^3$ |
|---|---|---|
| cyclopropyl | H | C$_2$H$_5$ |
| cyclopropyl | H | C$_3$H$_7$-n |
| cyclopropyl | H | C$_4$H$_9$-n |
| cyclopropyl | H | C$_5$H$_{11}$-n |
| cyclopropyl | H | C$_6$H$_{13}$-n |
| cyclopropyl | H | C$_7$H$_{15}$-n |
| cyclopropyl | H | C$_8$H$_{17}$-n |
| cyclopropyl | H | C$_{12}$—H$_{25}$-n |
| cyclopropyl | H | CH$_2$—C$_4$H$_9$-n |
| cyclopropyl | H | CH$_2$CH(CH$_3$)C$_2$H$_5$ |
| cyclopropyl | H | CH$_2$CH=CH$_2$ |
| cyclopropyl | Cl | C$_2$H$_5$ |
| cyclopropyl | Cl | C$_6$H$_{13}$-n |
| cyclopropyl | Cl | C$_8$H$_{17}$-n |
| cyclopropyl | Cl | C$_{12}$H$_{25}$-n |
| cyclopropyl | H | cyclopropyl |
| cyclopropyl | H | COCH$_3$ |
| cyclopropyl | H | COCH$_3$ HCl |
| cyclopropyl | H | COC$_2$H$_5$ HCl |
| cyclopropyl | H | COC$_2$H$_5$ |
| cyclopropyl | H | COC$_3$H$_7$-n |
| cyclopropyl | H | COC$_3$H$_7$-i |
| cyclopropyl | H | COC$_4$H$_9$-t HCl |
| cyclopropyl | H | COC$_4$H$_9$-n |
| cyclopropyl | H | COC$_6$H$_{13}$-n |
| cyclopropyl | H | COC$_{11}$—H$_{23}$-n |
| cyclopropyl | COCH$_3$ | COC$_2$H$_5$ |
| cyclopropyl | COC$_3$H$_7$-n | COC$_6$H$_{13}$-n |
| cyclopropyl | COCH$_3$ | COC$_3$H$_7$-n |
| cyclopropyl | COC$_2$H$_5$ | COC$_3$H$_7$-n |
| cyclopropyl | H | COcyclopropyl |
| cyclopropyl | COcyclopropyl | COcyclopropyl |
| cyclopropyl | COCH$_3$ | COCH$_3$ |
| isopropyl | H | H |
| isopropyl | H | COCH$_3$ |
| isopropyl | H | COC$_3$H$_7$-n |
| cyclopropyl | H | CONHCH$_3$ |
| cyclopropyl | H | CONHC$_3$H$_7$-i |
| cyclopropyl | CONHCH$_3$ | CONHCH$_3$ |
| cyclopropyl | H | SCNHCH$_3$ |
| cyclopropyl | H | CONHCH$_2$CH=CH$_2$ |
| cyclopropyl | CONHCH$_2$CH=CH$_2$ | CONHCH$_2$CH=CH$_2$ |
| cyclopropyl | CSNHCH$_3$ | CSNHCH$_3$ |

Here, particular mention may be made of cyromazine and dicylanil.

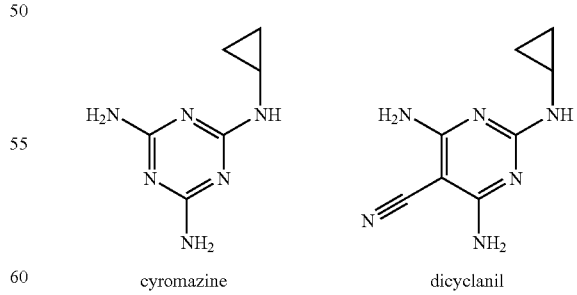

cyromazine      dicyclanil

The amounts of the active combination compounds which, if appropriate, may be employed in addition to the pyrethrins/pyrethroids can be varied within wide limits from 0.05 to 25%, where the amounts in the range of from 0.1 to 15.0% are particularly preferred and the amounts in the range of from 0.5 to 10.0% are very particularly preferred. Here, percentages are to be understood as percentages by weight, based on the finished preparation.

Particular preference is given to combinations of the pyrethroids and pyrethrins, in particular α-cyanopyrethroids, preferably flumethrin, cyfluthrin and β-cyfluthrin, with neonicotinoids, in particular imidacloprid, thiamethoxam, clothianidin, nitenpyram, acetamiprid and thiacloprid, or with spinosyns, in particular spinosad.

Of course, it is possible to add further synergists such as piperonyl butoxide, tributyl phosphite and sesame oil to the preparations according to the invention. These synergists are described, for example, in EP-A 413 610.

Stabilizers and antioxidants which may be mentioned are sulphites or metabisulphites, such as potassium metabisulphite; organic acids, such as citric acid, ascorbic acid; phenols, butylhydroxytoluene, butylhydroxyanisole, tocopherol. Preference is given to the organic acids citric acid and malic acid. Very particularly preferred stabilizers are citric acid and butylhydroxytoluene. Their proportion may be varied widely in the range of from 0.05 to 2.5% by weight, particular preference being given to amounts in the range of from 0.075 to 0.15% by weight. In spray formulations, the lower limit of the customary concentrations is lower, in general about 0.01% by weight; preferably, in spray formulations, the concentrations are from 0.03 to 0.1% by weight.

To prepare the preparations according to the invention, it is possible to use aromatic alcohols, such as benzyl alcohol, cyclic carbonates, such as propylene carbonate and ethylene carbonate, pyrrolidones, such as pyrrolid-2-one, N-methylpyrrolidone, N-octylpyrrolidone, N-butylpyrrolidone, low-boiling alcohols, such as isopropanol, ethanol, higher alcohols, such as N-octyl alcohol, lanolin alcohol and n-butanol, cyclic and acyclic ketones, such as acetone, methyl ethyl ketone and cyclohexanone, glycols, such as ethylene glycol and propylene glycol, aliphatic cyclic or acyclic ethers, such as tetrahydrofurfuryl alcohol, diethylene glycol monoethyl ether, dipropylene glycol monopropyl ether and glycofurol, aliphatic or aromatic fatty acid esters, such as isopropyl myristate, isopropyl palmitate and benzyl benzoate, triglycerides based on oleic acid, palmitic acid, linoleic acid, stearic acid, caprylic acid and caprinic acid, lactones, such as butyrolactone, and their mixtures with one another. Particular preference is given to using carbonates, alcohols and pyrrolidones.

The proportion of solvent in the compositions according to the invention depends, of course, on the type and amount of the further constituents, and accordingly, it may vary considerably. Usually, the solvent content is at least 10% by weight, preferably at least 50% by weight, particularly preferably at least 60% by weight.

Furthermore, the formulations according to the invention may comprise polymeric and/or oligomeric surface-active neutral, cationic or anionic auxiliaries, such as polyvinylpyrrolidone, polyvinyl alcohol, polyoxyethylene or polyoxypropylene sorbitan acid esters, polyoxyethylene stearates or products of the reaction of the phenoxyphenols and/or methoxysilanes with ethylene oxide and propylene oxide, alkali metal and alkaline earth metal salts of the carboxylic and sulphonic acids, quaternary ammonium salts, such as benzylammonium chloride—if appropriate also in combination with one another—in amounts of from 0.1 to 5% by weight, preferably from 0.2 to 2.0% by weight, to improve flowability, viscosity and affinity to hair and fur.

Odour-masking agents are, for example, mixtures of organic fatty acid esters. In the formulations according to the invention, they are preferably present in amounts of from 0.1 to 2% by weight.

If the compositions according to the invention are used in the form of an aerosol spray, a presolution is, together with a propellant, filled into customary spray cans or the like. Customary propellants or propellant gases are, for example, gaseous hydrocarbons, such as propane, butane (preference is given to a propane/butane mixture, in particular in a ratio of 80:20), fluorocarbons, chlorofluorocarbons, $N_2O$, $CO_2$, nitrogen.

Surprisingly, the liquid formulations according to the invention have an excellent storage stability of several years in all climate zones, and excellent skin friendliness and user compatibility and environmental compatibility. Surprisingly, they are also highly suitable for being filled into and sold in storage-critical single dose plastic tubes which usually consist of polypropylene, have a wall thickness of 300-500 μm and a filling volume of 1.0 to 4.0 ml.

Such single dose plastic tubes filled with the compositions according to the invention accordingly also form part of the subject-matter of the present invention.

Additionally, the liquid formulations according to the invention have an unexpected synergistic, i.e. activity-enhancing, effect when pyrethroids/pyrethrins are used as active compound.

The compositions according to the invention are environmentally friendly and, owing to their very low toxicity, user-friendly.

Having favourable homeotherm toxicity, the compositions according to the invention are suitable for controlling parasitic insects, in particular fleas and ticks, encountered on animals, in particular homeotherms, particularly preferably mammals. These animals may be domestic animals and useful animals and also zoo animals, laboratory animals, test animals and pets. The compositions according to the invention are active against all or individual stages of development of the pests and against resistant and normally sensitive test species.

The pests include:
from the order of the Anoplura, for example, *Haematopinus* spp., *Linognathus* spp., *Solenopotes* spp., *Pediculus* spp., *Pthirus* spp.;
from the order of the Mallophaga, for example, *Trimenopon* spp., *Menopon* spp., *Eomenacanthus* spp., *Menacanthus* spp., *Trichodectes* spp., *Felicola* spp., *Damalinea* spp., *Bovicola* spp;
from the order of the Diptera, suborder Brachycera, for example, *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Chrysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp.
from the order of the Diptera, suborder Nematocera, for example, *Culex* spp., *Aedes* spp., *Anopheles* spp., *Culicoides* spp., *Phlebotomus* spp., *Simulium* spp.
from the order of the Siphonaptera, for example, *Ctenocephalides* spp., *Echidnophaga* spp., *Ceratophyllus* spp., *Pulex* spp.
from the order of the Metastigmata, for example, *Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.;

from the order of the Mesostigmata, for example, *Dermanyssus* spp., *Ornithonyssus* spp., *Pneumonyssus* spp.
from the order of the Prostigmata, for example, *Cheyletiella* spp., *Psorergates* spp., *Myobia* spp., *Demodex* spp., *Neotrombicula* spp.;
from the order of the Astigmata, for example, *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidocoptes* spp., *Cytodites* spp., *Laminosioptes* spp.

Particular emphasis may be given to the action against *Siphonaptera*, in particular against fleas and ticks.

The useful and breeding animals include mammals, such as, for example, cattle, horses, sheep, pigs, goats, camels, water buffalo, donkeys, rabbits, fallow deer, reindeer, fur-bearing animals, such as, for example, mink, chinchilla, raccoon, birds, such as, for example, hens, geese, turkeys, ducks.

The laboratory animals and test animals include mice, rats, guinea pigs, golden hamsters, dogs and cats.

The pets include dogs and cats.

Particular emphasis is given to application on cat and dog.

Application can take place both prophylactically and therapeutically.

In principle, the novel liquid formulations according to the invention are suitable for spot-on, pour-on and pump spray and also aerosol spray applications. The preferred application forms are pour-on and pump spray. The spot-on application is very particularly preferred.

To prepare the liquid formulation according to the invention, appropriate amounts of the desired components are mixed with one another using, for example, conventional stirring tanks or other suitable apparatus.

If required for the ingredients, the operations can also be carried out under a protective atmosphere or by other methods where oxygen is excluded.

The examples below serve to illustrate the invention:

EXAMPLES

Example 1a

A homogeneous spot-on formulation (100 ml) comprising

| | |
|---|---|
| 1.00 g | flumethrin |
| 10.00 g | imidacloprid |
| 40.00 g | MGK 264 |
| 48.00 g | N-methylpyrrolidone//THFA (tetrahydrofurfuryl alcohol) (70:30) |
| 0.10 g | citric acid |
| 0.10 g | BHT (butylhydroxytoluene) |

Example 1b

A homogeneous spot-on formulation (100 ml) comprising

| | |
|---|---|
| 0.50 g | flumethrin |
| 10.00 g | imidacloprid |
| 40.00 g | MGK 264 |
| 48.50 g | N-methylpyrrolidone//THFA (tetrahydrofurfuryl alcohol) (70:30) |
| 0.10 g | citric acid |
| 0.10 g | BHT (butylhydroxytoluene) |

Example 2a

A homogeneous spot-on formulation (100 ml) comprising

| | |
|---|---|
| 0.50 g | flumethrin |
| 10.00 g | imidacloprid |
| 10.00 g | MGK 264 |
| 59.40 g | N-methylpyrrolidone//THFA (tetrahydrofurfuryl alcohol) (70:30) |
| 25.00 g | Miglyol 812 |
| 0.10 g | citric acid |
| 0.10 g | BHT (butylhydroxytoluene) |

Example 2b

A homogeneous spot-on formulation (100 ml) comprising

| | |
|---|---|
| 0.35 g | flumethrin |
| 10.00 g | imidacloprid |
| 10.00 g | MGK 264 |
| 59.55 g | N-methylpyrrolidone//THFA (tetrahydrofurfuryl alcohol) (70:30) |
| 25.00 g | Miglyol 812 |
| 0.10 g | citric acid |
| 0.10 g | BHT (butylhydroxytoluene) |

Example 2c

A homogeneous spot-n formulation (100 ml) comprising

| | |
|---|---|
| 0.20 g | flumethrin |
| 10.00 g | imidacloprid |
| 10.00 g | MGK 264 |
| 59.70 g | N-methylpyrrolidone//THFA (tetrahydrofurfuryl alcohol) (70:30) |
| 25.00 g | Miglyol 812 |
| 0.10 g | citric acid |
| 0.10 g | BHT (butylhydroxytoluene) |

Example 3

A homogeneous spot-on formulation (100 ml) comprising

| | |
|---|---|
| 0.50 g | flumethrin |
| 10.00 g | imidacloprid |
| 20.00 g | MGK 264 |
| 50.00 g | N-methylpyrrolidone//propylene carbonate (70:30) |
| 13.75 g | Miglyol 812 |
| 0.1 g | citric acid |
| 0.1 g | BHT (butylhydroxytoluene) |

Example 4

A homogeneous spot-on formulation (100 ml) comprising

| | |
|---|---|
| 0.50 g | flumethrin |
| 10.00 g | imidacloprid |
| 10.00 g | MGK 264 |
| 72.85 g | benzyl alcohol |
| 14.48 g | propylene carbonate |
| 0.1 g | citric acid |
| 0.1 g | BHT (butylhydroxytoluene) |

Example 5

A homogeneous spot-on formulation (100 ml) comprising

| | |
|---|---|
| 0.35 g | flumethrin |
| 10.00 g | imidacloprid |
| 10.00 g | MGK 264 |
| 72.70 g | benzyl alcohol |
| 14.33 g | propylene carbonate |
| 0.1 g | citric acid |
| 0.1 g | BHT (butylhydroxytoluene) |

Example 6

A homogeneous spot-on formulation (100 ml) comprising

| | |
|---|---|
| 0.35 g | flumethrin |
| 10.00 g | imidacloprid |
| 15.00 g | MGK 264 |
| 65.46 g | benzyl alcohol |
| 12.94 g | propylene carbonate |
| 0.1 g | citric acid |
| 0.1 g | BHT (butylhydroxytoluene) |
| 5.00 g | water |

Example 7

A homogeneous spot-on formulation (100 ml) comprising

| | |
|---|---|
| 0.35 g | flumethrin |
| 10.00 g | imidacloprid |
| 15.00 g | MGK 264 |
| 44.98 g | N-methylpyrrolidone |
| 32.08 g | THFA |
| 0.1 g | citric acid |
| 0.1 g | BHT (butylhydroxytoluene) |

In addition to the particularly preferred spot-on application, a preferred distribution of the active compound combinations mentioned by spraying using a pump spray or aerosol spray is also possible. For this purpose, other formulations are required, which are described in the preparation examples below.

Example 8

A pump spray formulation (250 ml) comprising

| | |
|---|---|
| 2.50 g | imidacloprid |
| 0.125 g | flumethrin |
| 5.00 g | MGK 264 |
| 0.125 g | BHT |
| 0.125 g | citric acid |
| 20.80 g | benzyl alcohol |
| 4.125 g | propylene carbonate |
| 25.00 g | water |
| 154.63 g | isopropanol |

For application of the formulation in the activity studies on dogs and cats, a conventional pump spray nozzle with D(v0.5) of about 65 µm was used.

Example 9

A pump spray formulation (250 ml) comprising

| | |
|---|---|
| 2.50 g | imidacloprid |
| 0.125 g | flumethrin |
| 5.00 g | MGK 264 |
| 0.125 g | BHT |
| 0.125 g | citric acid |
| 20.80 g | benzyl alcohol |
| 4.125 g | propylene carbonate |
| 25.00 g | water |
| 154.63 g | isopropanol |

For application of the formulation in the activity studies on dogs and cats, a conventional pump spray nozzle with D(v0.5) of about 65 µm was used.

Example 10a

A pump spray formulation (250 ml) comprising

| | |
|---|---|
| 2.50 g | thiamethoxam |
| 0.125 g | flumethrin |
| 5.00 g | MGK 264 |
| 0.125 g | BHT |
| 0.125 g | citric acid |
| 20.80 g | benzyl alcohol |
| 4.125 g | propylene carbonate |
| 25.00 g | water |
| 154.63 g | isopropanol |

For application of the formulation in the activity studies on dogs and cats, a conventional pump spray nozzle with D(v0.5) of about 65 µm was used.

Example 10b

A pump spray formulation (250 ml) comprising

| | |
|---|---|
| 2.50 g | thiacloprid |
| 0.125 g | flumethrin |
| 5.00 g | MGK 264 |
| 0.125 g | BHT |
| 0.125 g | citric acid |
| 20.80 g | benzyl alcohol |
| 4.125 g | propylene carbonate |
| 25.00 g | water |
| 154.63 g | isopropanol |

For application of the formulation in the activity studies on dogs and cats, a conventional pump spray nozzle with D(v0.5) of about 65 µm was used.

Example 11

A 250 ml presolution for preparing customary aerosol sprays, comprising

| | |
|---|---|
| 2.00 g | thiamethoxam |
| 0.15 g | flumethrin |
| 5.00 g | MGK 264 |
| 0.125 g | BHT |
| 0.025 g | citric acid |

-continued

| | |
|---|---|
| 36.475 g | benzyl alcohol |
| 7.225 g | propylene carbonate |
| 25.00 g | water |
| 141.25 g | isopropanol |

140 g of the presolution according to Example II and 60 g of a propane/butane propellant mixture (propane:butane=80:20) were filled into a conventional tin plate aerosol can, which was fitted with a customary aerosol nozzle from Kosmos and then used for carrying out activity studies on dogs and cats.

Example 12

A 250 ml presolution for preparing customary aerosol sprays, comprising

| | |
|---|---|
| 2.00 g | imidacloprid |
| 0.15 g | flumethrin |
| 5.00 g | MGK 264 |
| 0.125 g | BHT |
| 0.025 g | citric acid |
| 36.475 g | benzyl alcohol |
| 7.225 g | propylene carbonate |
| 25.00 g | water |
| 141.25 g | isopropanol |

140 g of the presolution according to Example 12 and 60 g of a propane/butane propellant mixture (propane:butane=80:20) were filled into a conventional tin plate aerosol can, which was fitted with a customary aerosol nozzle from Kosmos and then used for carrying out activity studies on dogs and cats.

Example 13

A 250 ml presolution for preparing customary aerosol sprays, comprising

| | |
|---|---|
| 2.00 g | thiacloprid |
| 0.15 g | flumethrin |
| 5.00 g | MGK 264 |
| 0.125 g | BHT |
| 0.025 g | citric acid |
| 36.475 g | benzyl alcohol |
| 7.225 g | propylene carbonate |
| 25.00 g | water |
| 141.25 g | isopropanol |

140 g of the presolution according to Example 13 and 60 g of a propane/butane propellant mixture (propane:butane=80:20) were filled into a conventional tin plate aerosol can, which was fitted with a customary aerosol nozzle from Kosmos and then used for carrying out activity studies on dogs and cats.

The aerosol nozzle from Kosmos used in Examples 11-13 is used for preparing commercial insecticide-containing aerosol sprays (for example Bolfo Flohschutz Spray, Bolfo Plus Spray from Bayer HealthCare AG D-51368 Leverkusen).

Further laboratory tests on the activity against ticks according to Examples 1, 2, 5 and 9 show that the above formulation according to the invention is highly active against ticks, is distinguished by its compatibility with target animal and user and suitable for controlling fleas and ticks on small animals.

A. Activity Against Fleas on Dogs

*Ctenocephalides felis*

On days −4 and −1, dogs are infested with about 100 adult unfed *Ctenocephalides felis* per dog. The fleas are placed on the neck of the animal.

On day 0, the success of the infestation on the dog is examined by checking the awake animal for fleas. The number of live fleas is noted.

After the fleas have been counted, the animals are treated. The dogs of the control group are not treated. The medicaments to be examined are administered to the animals dermally as a spot-on in an application rate of 0.1 ml/kg of body weight or as a spray in an application rate of 1-1.5 ml/kg of body weight. The application is carried out once on day 0. Only animals that are clinically healthy are used.

On day 1 and on day 2, all dogs are examined for live fleas. The results are noted with the crude data.

On days 7, 14, 21 and 28, all dogs are reinfested with about 100 adult unfed *Ctenocephalides felis* per dog. In each case one day after the reinfestation, all dogs are checked for live fleas. The results are noted with the crude data.

A formulation is considered to be highly active if, on day 1 and in each case on the second day after reinfestation, an efficacy of >95% is found, and this action persists for at least 3-4 weeks.

The efficacy is calculated using a modified formula according to Abbott:

$$\text{Efficacy}\% = \frac{\phi \text{ number of fleas } CG - \phi \text{ number of fleas } TG}{\phi \text{ number of fleas } CG} \times 100$$

CG: Control group
TG: Treatment group

The medicaments of Formulation Examples 1 to 5, applied as a spot-on at a dosage of 0.1 ml/kg, were found to be highly effective against *Ctenocephalides felis*.

The medicaments of Formulation Examples 8 to 10, applied as a spray at a dosage of 1-1.5 ml/kg, were found to be highly effective against *Ctenocephalides felis*.

B. Efficacy Against Ticks (*Rhipicefalus sanguineus, Haemaphysalis leachi*) on Dogs In each case on days −4 and −1, dogs are sedated using 2% Rompun® (Bayer AG, active compound: xylazine hydrochloride) (0.1 ml/kg of body weight). Once all dogs have been sedated (after about 10-15 minutes), they are transferred to transport boxes, and 50 *Rhipicefalus sanguineus* or *Haemaphysalis leachi* (25 ♀. 25 ♂) per dog are applied to the neck of the animal. After about ½ hours, the animals are retransferred from the transport box into the cage.

On day 0, the success of the infestation on the dog is examined by checking the awake animal for ticks. An intensive search is carried out in the region of the head and the ears, including the folds of the ears, in the region of the neck, on the lower abdomen, on the lower breast, on the flank and in between the toes and the limbs. The number of sucking live ticks is noted. Dead ticks are removed.

After the ticks have been counted, the animals are treated. The dogs of the control group are not treated. The medicaments to be examined are administered to the animals dermally, as a spot-on, at 0.1 ml/kg of body weight or as a spray at 1-1.5 ml/kg of body weight. Application is carried out once on day 0. Only animals which are clinically healthy are used.

On day 1 and on day 2, all dogs are checked for living and dead sucking ticks. The results are noted with the crude data. On day 2, all living and dead ticks are removed from the dog.

On days 7, 14, 21 and 28, all dogs are reinfested with in each case 50 *Rhipicefalus sanguineus* or *Haemaphysalis leachi* (25 ♀, 25 ♂) per dog. In each case two days after the reinfestation, all dogs are checked for living and dead sucking ticks. The results are noted with the crude data. On the second day after the reinfestation, all living and dead ticks are removed from the dog.

A formulation is considered to be highly active if, on day 2 and in each case on the second day after reinfestation, an efficacy of >90% is found, and this action persists for at least 3 weeks.

For calculating the efficacy, a modified formula according to Abbott is used:

$$\text{Efficacy\%} = \frac{\phi \text{ number of ticks } CG - \phi \text{ number of ticks } TG}{\phi \text{ number of ticks } CG} \times 100$$

CG: Control group
TG: Treatment group

The medicaments according to Formulation Examples 1 to 5, applied as a spot-on at a dosage of 0.1 ml/kg, were found to be highly effective against *Rhipicephalus sanguineus*.

The medicaments according to Formulation Examples 8 to 10, applied as a spray at a dosage of 1-1.5 ml/kg, were found to be highly effective against *Rhipicephalus sanguineus* and *Haemaphysalis leachi*.

C. Activity Against Fleas (*Ctenocephalides felis*) on Cats

On day −1, cats are infested with about 100 adult unfed *Ctenocephalides felis* per cat. The fleas are placed onto the neck of the animal.

On day 0, the success of the infestation on the cat is examined by checking the awake animal for fleas. The number of live fleas is noted.

After the fleas have been counted, the animals are treated. The cats of the control group are not treated. The medicaments to be examined according to Examples 1 to 4 are administered to the animals dermally as a spot-on in an application rate of 0.1 ml/kg of body weight. The application is carried out once on day 0. Only animals that are clinically healthy are used.

On day 2, all cats are examined for live fleas. The results are noted with the crude data.

On days 6, 13, 20 and 27, all cats are reinfested with about 100 adult unfed *Ctenocephalides felis*. In each case two days after the reinfestation, all cats are checked for live fleas. The results are noted with the crude data.

A formulation is considered to be highly active if, on day 2 and in each case on the second day after reinfestation, an efficacy of >95% is found, and this action persists for at least 34 weeks.

The efficacy is calculated using a modified formula according to Abbott:

$$\text{Efficacy\%} = \frac{\phi \text{ number of fleas } CG - \phi \text{ number of fleas } TG}{\phi \text{ number of fleas } CG} \times 100$$

CG: Control group
TG: Treatment group

The medicaments of Formulation Examples 1 to 5, applied as a spot-on at a dosage of 0.1 ml/kg, were found to be highly effective against *Ctenocephalides felis*.

D. Activity Against Ticks (*Haemaphysalis leachi*) on Cats

In each case on day −2, cats are sedated using a mild sedative (acepromazine maleat). Once all cats have been sedated (after about 10-15 minutes), 30 *Haemaphysalis leachi* (15♀, 15§) are applied to the neck of each animal.

On day −1, the success of the infestation on the cats is examined by checking the awake animals for ticks. An intensive search is carried out in the region of the head and the ears, in the region of the neck, on the lower abdomen, on the lower breast, on the flank and on the limbs. The number of sucking live ticks is noted. Dead ticks are removed.

After the ticks have been counted, the animals are divided into groups. Treatment is carried out on day 0. The cats of the control group are not treated. The medicaments to be examined are administered to the animals dermally as a spot-on at 0.1 ml/kg of body weight. Application is carried out once on day 0. Only animals which are clinically healthy are used.

On day 2, all cats are checked for living and dead sucking ticks. The results are noted with the crude data. All living and dead ticks are removed from the cat.

On days 6, 13, 20 and 27, all cats are reinfested with in each case 30 Haemaphysalis leachi (15♀, 15♂) per cat. In each case two days after the reinfestation, all cats are checked for living and dead sucking ticks. The results are noted with the crude data. On the second day after the reinfestation, all living and dead ticks are removed from the cat.

A formulation is considered to be highly active if, on day 2 and in each case on the second day after reinfestation, an efficacy of >90% is found, and this action persists for at least 3 weeks.

For calculating the efficacy, a modified formula according to Abbott is used:

$$\text{Efficacy\%} = \frac{\phi \text{ number of ticks } CG - \phi \text{ number of ticks } TG}{\phi \text{ number of ticks } CG} \times 100$$

CG: Control group
TG: Treatment group

The medicaments according to Formulation Examples 1 to 4, applied as a spot-on at a dosage of 0.1 ml/kg, were found to be highly effective against *Haemaphysalis leachi*.

E. Activity Against Fleas and Ticks Over a Period of 4 to 5 Weeks

The activity of the compositions according to the invention against fleas and ticks was tested over a period of four to five weeks. The test was carried out analogously to the description given under items A to D.

TABLE 1

Activity of the compositions of Examples 1a and 1b against fleas and ticks on dogs

| 1st Infestation: | 2nd Infestation: | d 0 | Appl. Vol. | Week 0 d 1 efficacy | | Week 0 d 2 efficacy | | 3rd Infestation: | Week 1 d 9 efficacy | | 4th Infestation: | Week 2 d 16 efficacy | |
|---|---|---|---|---|---|---|---|---|---|---|---|---|---|
| Day −4 | Day −1 | Treatment | ml/kg | CF % | RS % | CF % | RS % | Day 7 | CF % | RS % | Day 14 | CF % | RS % |
| | | Example 1a | 0.10 | 100 | 81 | 100 | 94 | | 100 | 100 | | 100 | 100 |
| | | Example 1b | 0.10 | 100 | 67 | 100 | 94 | | 100 | 96 | | 100 | 99 |

TABLE 1-continued

Activity of the compositions of Examples 1a and 1b against fleas and ticks on dogs

| Treatment | d 0 | 5th Appl. Vol. ml/kg | Infes- tation: Day 21 | Week 3 d 23 efficacy CF % | RS % | 6th Infes- tation: Day 28 | Week 4 d 30 efficacy CF % | RS % | 7th Infes- tation: Day 35 | Week 5 d 37 efficacy CF % | RS % |
|---|---|---|---|---|---|---|---|---|---|---|---|
| Example 1a | | 0.10 | | 100 | 98 | | 97 | 100 | | 95 | 95 |
| Example 1b | | 0.10 | | 100 | 100 | | 98 | 99 | | 92 | 98 |

Appl. Vol. = Volume applied in ml/kg of body weight
CF % = Activity against *Ctenocephalides felis* fleas in %, calculated by determination of the geometrical mean compared to an untreated control group
RS % = Activity against *Rhipicephalus sanguineus* ticks in %, calculated by determination of the geometrical mean compared to an untreated control group
d = Day

TABLE 2

Activity of the compositions of Examples 2a, 2b and 2c against fleas and ticks on dogs

| 1st Infes- tation: Day −4 | 2nd Infes- tation: Day −1 | d 0 Treatment | Appl. Vol. ml/kg | Week 0 d 1 efficacy CF % | RS % | d 2 efficacy CF % | RS % | 3rd Infes- tation: Day 7 | Week 1 d 8 efficacy CF % | RS % | d 9 efficacy CF % | RS % | 4th Infes- tation: Day 14 | Week 2 d 16 efficacy CF % | RS % |
|---|---|---|---|---|---|---|---|---|---|---|---|---|---|---|---|
| | | Example 2a | 0.10 | 93 | 72 | 100 | 94 | | 100 | 100 | 100 | 100 | | 99 | 99 |
| | | Example 2b | 0.10 | 96 | 61 | 100 | 90 | | 100 | 97 | 99 | 98 | | 94 | 92 |
| | | Example 2c | 0.10 | 98 | 60 | 100 | 98 | | 100 | 100 | 100 | 99 | | 97 | 94 |

| Treatment | d 0 | 5th Appl. Vol. ml/kg | Infes- tation: Day 21 | Week 3 d 23 efficacy CF % | RS % | 6th Infes- tation: Day 28 | Week 4 d 30 efficacy CF % | RS % | 7th Infes- tation: Day 35 | Week 5 d 37 efficacy CF % | RS % |
|---|---|---|---|---|---|---|---|---|---|---|---|
| Example 2a | | 0.10 | | 100 | 100 | | 79 | 90 | | 83 | 89 |
| Example 2b | | 0.10 | | 75 | 85 | | 56 | 77 | | 13 | 33 |
| Example 2c | | 0.10 | | 94 | 95 | | 84 | 82 | | 58 | 54 |

Appl. Vol. = Volume applied in ml/kg of body weight
CF % = Activity against *Ctenocephalides felis* fleas in %, calculated by determination of the geometrical mean compared to an untreated control group
RS % = Activity against *Rhipicephalus sanguineus* ticks in %, calculated by determination of the geometrical mean compared to an untreated control group
d = Day

TABLE 3

Activity of the compositions of Examples 2b and 5 against fleas and ticks on cats

| 1st Infes- tation: Day −2 | d 0 Treatment | Appl. Vol. ml/kg | Week 0 d 2 efficacy CF % | HL % | 2nd Infes- tation: Day 7 | Week 1 d 8 efficacy CF % | HL % | 3rd Infes- tation: Day 14 | Week 2 d 15 efficacy CF % | HL % |
|---|---|---|---|---|---|---|---|---|---|---|
| | Example 2b | 0.10 | 100 | 35 | | 100 | 67 | | 97 | 86 |
| | Example 5 | 0.10 | 100 | 24 | | 100 | 93 | | 100 | 91 |

| Treatment | d 0 | 4th Appl. Vol. ml/kg | Infes- tation: Day 21 | Week 3 d 23 efficacy CF % | HL % | 5th Infes- tation: Day 28 | Week 4 d 29 efficacy CF % | HL % |
|---|---|---|---|---|---|---|---|---|
| Example 2b | | 0.10 | | 91 | 80 | | 84 | 71 |
| Example 5 | | 0.10 | | 99 | 91 | | 94 | 97 |

Appl. Vol. = Volume applied in ml/kg of body weight
CF % = Activity against *Ctenocephalides felis* fleas in %, calculated by determination of the geometrical mean compared to an untreated control group
HL % = Activity against *Haemaphysalis leachi* ticks in %, calculated by determination of the geometrical mean compared to an untreated control group
d = Day

TABLE 4

Activity of the compositions of Example 9 against fleas and ticks on dogs

| 1st Infestation: Day −4 | 2nd Infestation: Day −1 | d 0 Treatment | Appl. Vol. ml/kg | Parasite | Week 0 d 2 efficacy | 3rd Infestaion: Day 7 | Week 1 d 8 efficacy | 4th Infestation: Day 14 | Week 2 d 14 efficacy |
|---|---|---|---|---|---|---|---|---|---|
| | | Example 9 | 1.30 | CF | 100 | | 100 | | 100 |
| | | | | HL | 89 | | 99 | | 98 |
| | | | | RS | 87 | | 99 | | 100 |

| | | d 0 Treatment | Appl. Vol. ml/kg | Parasite | 5th Infestation: Day 21 | Week 3 d 21 efficacy | 6th Infestation: Day 28 | Week 4 d 28 efficacy | 7th Infestation: Day 35 | Week 5 d 35 efficacy |
|---|---|---|---|---|---|---|---|---|---|---|
| | | Example 9 | 1.30 | CF | | 100 | | 100 | | 100 |
| | | | | HL | | 94 | | 89 | | 74 |
| | | | | RS | | 98 | | 96 | | 91 |

Appl. Vol. = Volume applied in ml/kg of body weight
CF % = Activity against *Ctenocephalides felis* fleas in %, calculated by determination of the geometrical mean compared to an untreated control group
HL % = Activity against *Haemaphysalis leachi* ticks in %, calculated by determination of the geometrical mean compared to an untreated control group
RS % = Activity against *Rhipicephalus sanguineus* ticks in %, calculated by determination of the geometrical mean compared to an untreated control group
d = Day

The invention claimed is:

1. A composition comprising:
   a. flumethrin; and,
   b. (2-(2-ethylhexyl)-3a,4,7,7a-tetrahydro-4,7-methano-1H-isoindole-1,3(2H)-dione
   wherein the amount of b is at least 20 fold more than a.

2. The composition of claim 1, further comprising a neonicotinoid insecticide.

3. The composition of claim 1, further comprising imidacloprid.

4. A method for controlling parasites comprising applying to an animal in need thereof an effective amount of a composition of claim 1.

* * * * *